(12) United States Patent
Kanazawa et al.

(10) Patent No.: US 12,357,402 B2
(45) Date of Patent: Jul. 15, 2025

(54) SURGICAL ROBOT

(71) Applicant: RIVERFIELD INC., Tokyo (JP)

(72) Inventors: Masao Kanazawa, Tokyo (JP); Satoshi Kano, Tokyo (JP); Nobuaki Yamamoto, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 378 days.

(21) Appl. No.: 17/885,123

(22) Filed: Aug. 10, 2022

(65) Prior Publication Data
US 2022/0378531 A1 Dec. 1, 2022

Related U.S. Application Data

(63) Continuation of application No. PCT/JP2021/000868, filed on Jan. 13, 2021.

(30) Foreign Application Priority Data

Feb. 12, 2020 (JP) ................................ 2020-021633

(51) Int. Cl.
*A61B 34/30* (2016.01)
(52) U.S. Cl.
CPC ........ *A61B 34/30* (2016.02); *A61B 2034/301* (2016.02)
(58) Field of Classification Search
CPC ........................... A61B 2034/301; A61B 34/30
See application file for complete search history.

(56) References Cited

U.S. PATENT DOCUMENTS

| 6,554,780 | B1 * | 4/2003 | Sampson ............... A61B 18/00 |
| | | | 600/560 |
| 11,147,575 | B2 * | 10/2021 | Ogata .................... B25J 13/082 |
| 2003/0191412 | A1 | 10/2003 | Sampson et al. |
| 2004/0215099 | A1 | 10/2004 | Sampson et al. |
| 2005/0143728 | A1 | 6/2005 | Sampson et al. |
| 2007/0039626 | A1 | 2/2007 | Schulz |

(Continued)

FOREIGN PATENT DOCUMENTS

| CN | 101313865 B | * | 1/2013 | ....... A61B 17/07207 |
| CN | 104363853 A | | 2/2015 | |

(Continued)

OTHER PUBLICATIONS

International Preliminary Search on Patentability with the translation of Written Opinion dated Aug. 11, 2022 from the International Bureau in International Application No. PCT/JP2021/000868.

(Continued)

*Primary Examiner* — Natalie Huls
*Assistant Examiner* — Nyla Gavia
(74) *Attorney, Agent, or Firm* — Sughrue Mion, PLLC

(57) ABSTRACT

A surgical robot includes an operating section that receives a pressure from a gas, a pressure generating device that generates the pressure, a pressure detector that detects a pressure supplied from the pressure generating device to the operating section, and a control device configured to implement an operation diagnosis device that makes a determination, using the pressure detected by the pressure detector, whether the operating section is operable, and that notifies a result of the determination.

10 Claims, 8 Drawing Sheets

(56) References Cited

U.S. PATENT DOCUMENTS

| | | | |
|---|---|---|---|
| 2010/0139436 A1 | 6/2010 | Kawashima et al. | |
| 2014/0222204 A1 | 8/2014 | Kawashima et al. | |
| 2014/0222208 A1 | 8/2014 | Kawashima et al. | |
| 2014/0303551 A1 | 10/2014 | Germain et al. | |
| 2015/0150637 A1 | 6/2015 | Iwasa | |
| 2018/0168667 A1 | 6/2018 | Germain et al. | |
| 2019/0125456 A1* | 5/2019 | Shelton, IV | A61B 17/072 |
| 2019/0143540 A1 | 5/2019 | Tanaka et al. | |
| 2020/0315640 A1 | 10/2020 | Germain et al. | |
| 2020/0405403 A1* | 12/2020 | Shelton, IV | A61B 17/3421 |

FOREIGN PATENT DOCUMENTS

| | | | | |
|---|---|---|---|---|
| EP | 1 997 439 A2 | 12/2008 | | |
| EP | 3505081 A1 * | 7/2019 | | A61B 17/0469 |
| EP | 3506509 A1 * | 7/2019 | | A61B 1/000094 |
| JP | 2003-513742 A | 4/2003 | | |
| JP | 2004-329763 A | 11/2004 | | |
| JP | 2009045429 A * | 3/2009 | | A61B 17/07207 |
| JP | 4291039 B2 * | 7/2009 | | |
| JP | 2013-220273 A | 10/2013 | | |
| JP | 5327687 B2 | 10/2013 | | |
| JP | 2017-080170 A | 5/2017 | | |
| JP | 2017-203504 A | 11/2017 | | |
| JP | 2018-102634 A | 7/2018 | | |
| JP | 2018-140206 A | 9/2018 | | |
| WO | 2013/187342 A1 | 12/2013 | | |
| WO | 2015/079775 A1 | 6/2015 | | |
| WO | 2017/094843 A1 | 6/2017 | | |

OTHER PUBLICATIONS

International Search Report of PCT/JP2021/000868 dated Mar. 30, 2021 [PCT/ISA/210].
Japanese Office Action of No. 2020-021633 dated Jul. 14, 2020.
Japanese Office Action of No. 2020-021633 dated Oct. 27, 2020.

* cited by examiner

SURGICAL ROBOT

CROSS-REFERENCE TO RELATED APPLICATION

This U.S. Application is a continuation of International Application No. PCT/JP2021/000868, filed Jan. 13, 2021, which is based on and priority from Japanese Patent Application No. 2020-021633 filed on Feb. 12, 2020 with the Japan Patent Office, and the contents of each of which being herein incorporated by reference in their entireties.

BACKGROUND

The present disclosure relates to a surgical robot used in endoscopic surgery.

Often surgical robots use pressure from gas to operate during surgery. However, it may be difficult to determine whether the pressure is too low or too high such that the operating section operates improperly.

SUMMARY

It is an aspect to provide a surgical robot that prevents inoperability in cases with too low pressure or too high pressure.

According to an aspect of one or more embodiments, there is provided a surgical robot comprising an operating section that receives a pressure from a gas to thereby operate; a pressure generating device that generates the pressure; a pressure detector that detects a pressure supplied from the pressure generating device to the operating section; and an operation diagnosis device that makes a determination, using the pressure detected by the pressure detector, whether the operating section is operable, and that notifies a result of the determination.

According to another aspect of one or more embodiments, there is provided a surgical robot comprising a pressure cylinder that receives a pressure from a gas, to thereby operate; a pressure generating device that generates the pressure; a pressure sensor that detects the pressure supplied from the pressure generating device to the pressure cylinder; a monitor; and an operation diagnosis device makes a determination whether the pressure detected by the pressure sensor meets a pressure requirement, and displays, on the monitor, a notification based on a result of the determination.

According to another aspect of one or more embodiments, there is provided a surgical robot comprising a pressure cylinder that receives a pressure from a gas, to thereby operate; a pressure generating device that generates the pressure; a plurality of pressure sensors that detect the pressure supplied from the pressure generating device to the pressure cylinder; a display; and an operation diagnosis device configured to: determine whether a first detected pressure from a first sensor meets a first pressure requirement, determine, based on the first detected pressure meeting the first pressure requirement and a confirmation button being manipulated, determine whether a driver controller is activated, determine, based on the determination of the driver controller being activated, whether a second detected pressure meets a second pressure requirement, and display, based on the second detected pressure meeting the second pressure requirement and the confirmation button being manipulated, a notification that the pressure cylinder is operable on the display.

BRIEF DESCRIPTION OF THE DRAWINGS

The above and/or other aspects will become apparent and more readily appreciated from the following description of various embodiments, taken in conjunction with the accompanying drawings of which.

DETAILED DESCRIPTION

Figure 1:
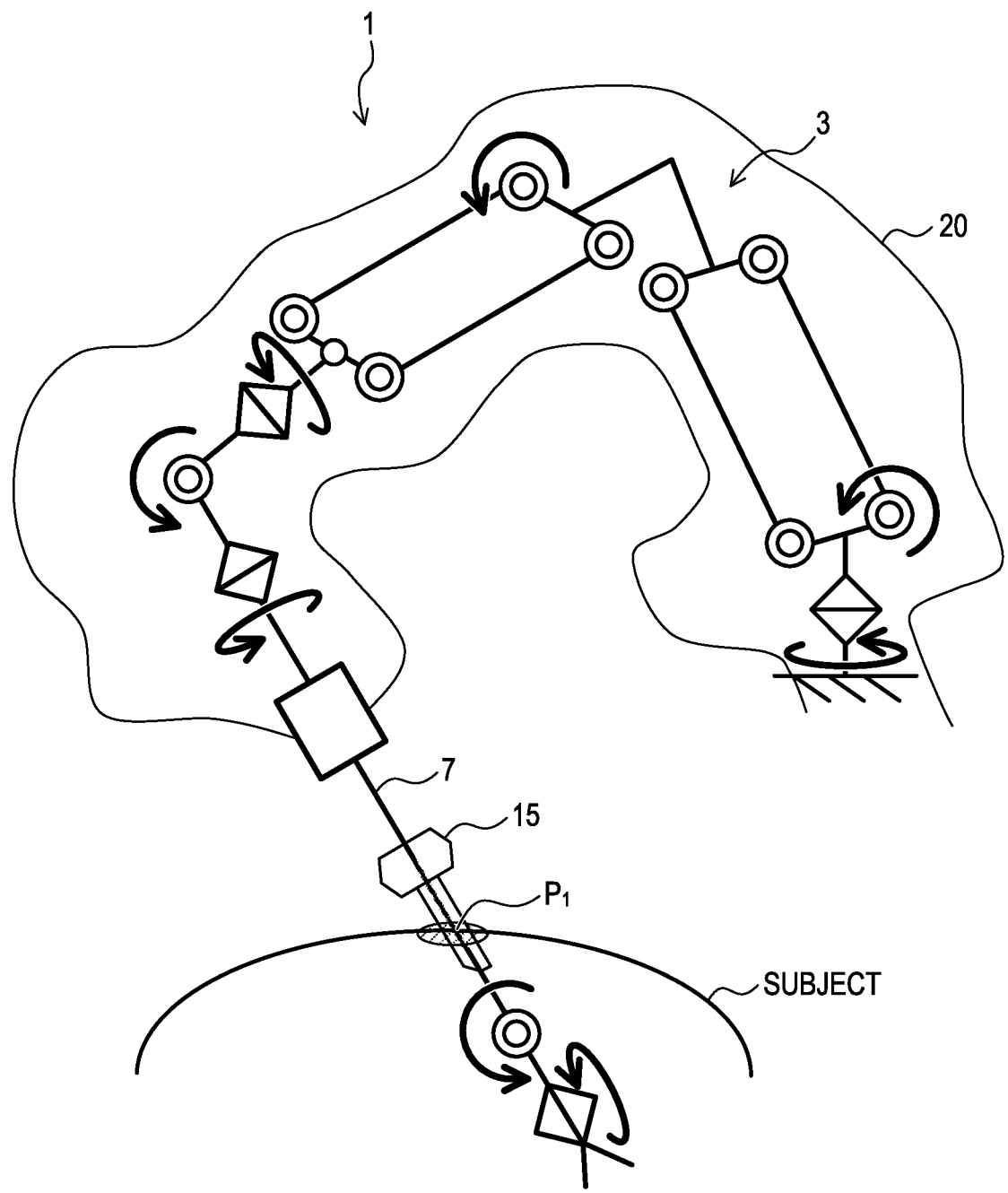
FIG. 1 is an external view of a surgical robot according to some embodiments.

For example, a related art surgical robot may include an operating section that receives a pressure from a gas to thereby operate. However, in the related art surgical robot, for example, in cases where the pressure is low, the operating section may operate improperly. Therefore, the present disclosure discloses an example of surgical robots that deal with the issue caused by the pressure.

In some embodiments, a surgical robot used in endoscopic surgery may comprise an operating section that receives a pressure from a gas to thereby operate; a pressure generating device that generates the pressure; a pressure detector that detects a pressure supplied from the pressure generating device to the operating section; and an operation diagnosis device that makes a determination, using the pressure detected by the pressure detector, whether the operating section is operable, and that notifies a result of the determination.

This configuration enables a user to readily know whether the surgical robot is in an operable state. The operation diagnosis device may determine, for example, at least one of a case where a pressure is so low that the surgical robot does not operate properly, and a case where a pressure is so high that the surgical robot does not operate properly.

Arrows indicating the directions, hatched lines, and so on in the drawings are made for easy understanding of relations between the drawings, and of the shapes of members or portions. Accordingly, the present disclosure is not limited by the directions shown in the drawings. The drawings with hatched lines provided thereon are not necessarily sectional views.

In regard at least to a member or a portion provided with a reference numeral and explained below, there is at least one of the member or portion unless it is specified. That is, two or more of such members or portions may be provided if the number is not specified to be only one. The surgical robot according to the present disclosure comprises, at least, components, such as the members or portions, with reference numerals and to be explained below, and structural portions illustrated.

1. Configuration of Surgical Robot

Figure 2:
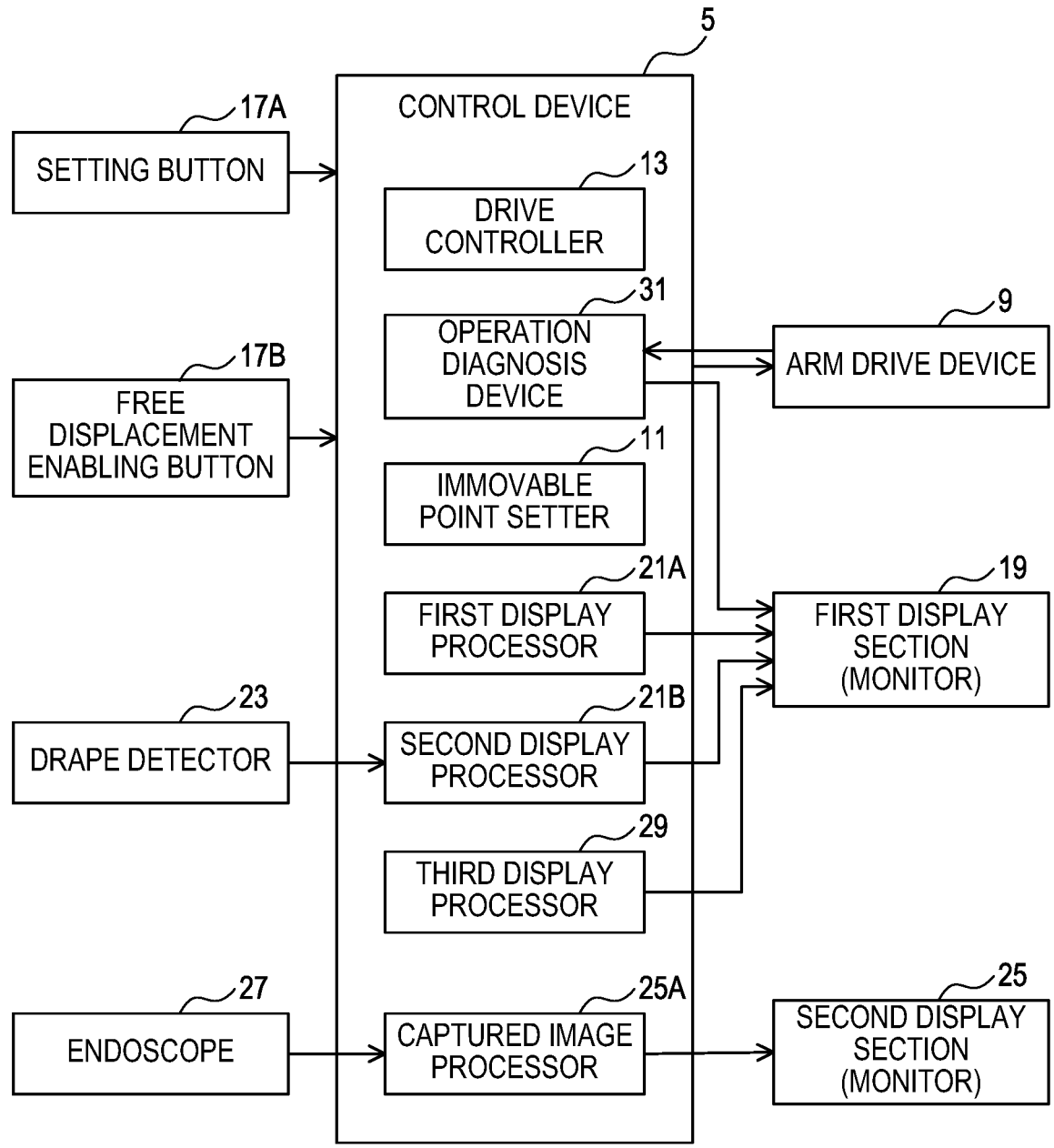
FIG. 2 is a block diagram of the surgical robot according to some embodiments.

FIG. 1 is an external view of a surgical robot according to some embodiments and FIG. 2 is a block diagram of the surgical robot according to some embodiments.

As shown in FIG. 2, a surgical robot 1 may comprise, in addition to a robot arm 3 (see FIG. 1), a control device 5, an arm drive device 9, a first display section 19, and a second display section 25.

<Robot Arm>

As shown in FIG. 1, the robot arm 3 is an example of an arm device holding a treatment tool 7. Specifically, the robot arm 3 is configured by a linkage mechanism including two or more joints. The linkage mechanism may change a position of a pivot.

The pivot is a position to be an immovable point when the robot arm 3 is operated, regardless of a state of the robot arm 3. The treatment tool 7 is an instrument, such as forceps, an electric scalpel, or the like, to be used during surgery.

The treatment tool 7 shown in FIG. 1 is forceps. The forceps is provided with a hand part at a distal end portion thereof. The hand part is provided for gripping, or pulling an organ, or the like. The robot arm 3 is covered with a drape 20. The drape may be tubular. The drape 20 is a non-woven fabric covering member having flexibility.

An endoscope 27 (see FIG. 2) is gripped by a second robot arm. Hereinafter, the treatment tool 7 and the endoscope 27 are collectively referred to as "surgical instrument". That is, the surgical instrument is a tool such as an endoscope, forceps, an electric scalpel, or the like to be used in endoscopic surgery.

<Arm Drive Device>

Figure 3:
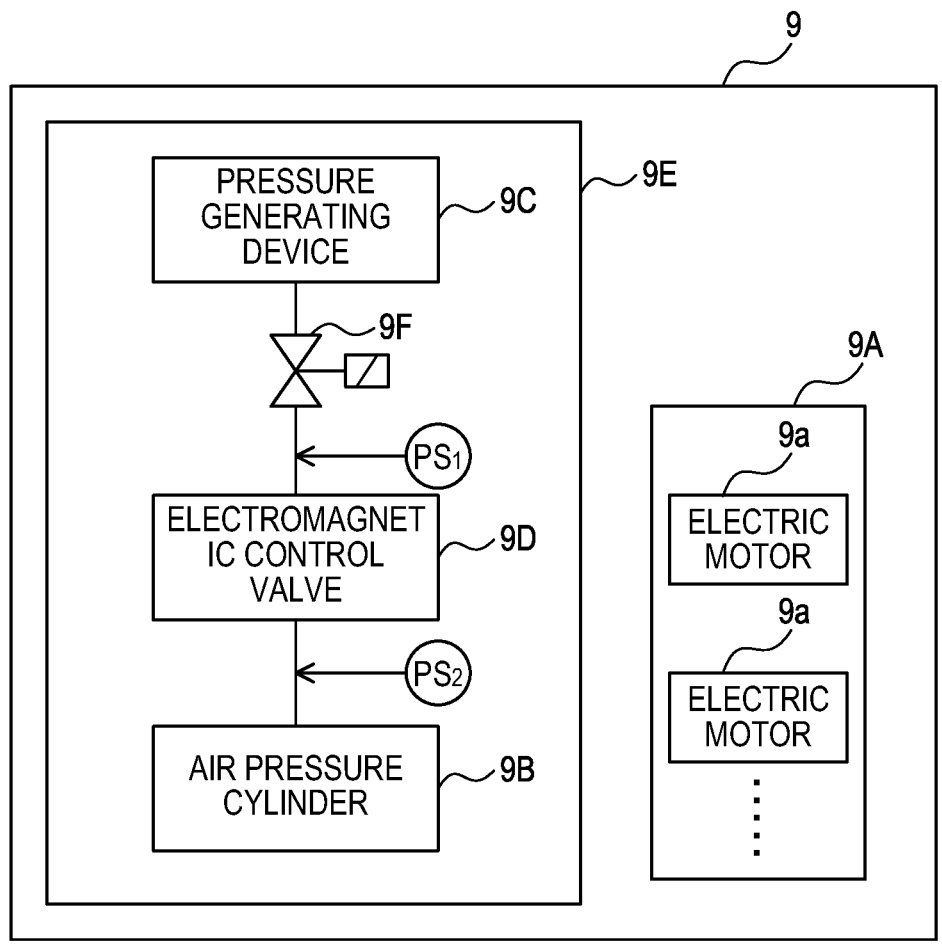
FIG. 3 is a block diagram of an arm drive device according to some embodiments.

The arm drive device 9 is an example of a driving device that drives the robot arm 3. As shown in FIG. 3, the arm drive device 9 according to some embodiments may comprise an electric actuator 9A and a pneumatic actuator 9E.

The electric actuator 9A is configured by at least one electric motor 9a to drive each joint portion. In some embodiments, the electric motor 9a is provided on each joint portion. The pneumatic actuator 9E applies some tension on a wire that drives the treatment tool 7. In some embodiments, the hand part in the forceps corresponds to an example of the treatment tool 7.

The pneumatic actuator 9E comprises an air pressure cylinder 9B, a pressure generating device 9C, and an electromagnetic control valve 9D. The pressure generating device 9C is a pressure supply source that supplies a compressed air to the air pressure cylinder 9B.

The air pressure cylinder 9B is an example of an operating section that receives air pressure to convert the received air pressure into the tension. The electromagnetic control valve 9D controls the air pressure to be supplied to the air pressure cylinder 9B, thereby to control an operation of the air pressure cylinder 9B.

The second robot arm is driven by a second arm drive device. The second arm drive device may have the same configuration as that of the arm drive device 9. The operation of the second arm drive device may be controlled in a similar manner to that of the arm drive device 9.

<Control Device>

As shown in FIG. 2, the control device 5 comprises an immovable point setter 11, a drive controller 13, a first display processor 21A, a second display processor 21B, a third display processor 29, a captured image processor 25A, and an operation diagnosis device 31. The control device 5 may be implemented by one or more microprocessors or hardware control logic.

The immovable point setter 11 recognizes a position of a site where a trocar 15 (see FIG. 1) is inserted in surgery (hereinafter, also referred to as "incision position"), and memorizes the recognized position as a pivot $P_1$.

Hereinafter, a series of operations in which the incision position is recognized by the immovable point setter 11 and the recognized incision positions are memorized, and the like is referred to as "immovable point setting". A state where the immovable point setting is enabled is referred to as "immovable point setting mode".

The trocar 15 is a tubular member to be inserted through an incised hole of a surgical subject. That is, a surgical instrument such as forceps (in other words, the treatment tool 7), the endoscope 27, and the like are inserted into a subject body through the trocar 15 inserted into an incision site.

<Drive Controller>

The drive controller 13 controls operation of the arm drive device 9, that is, the electric actuator 9A and the pneumatic actuator 9E (i.e., the electromagnetic control valve 9D), or the like. Specifically, the drive controller 13 receives a command signal output from a master-side input manipulation device to operate the arm drive device 9 in accordance with the received command signal.

At this time, the drive controller 13 utilizes the position of the pivot $P_1$ to control operation of the robot arm 3. Specifically, the drive controller 13 controls the operation of the electric actuator 9A such that a portion of the treatment tool 7 corresponding to the pivot $P_1$ remains immovable.

The operation of the second arm drive device is controlled by a second drive controller. The second drive controller operates the second robot arm as the pivot $P_1$ as an incision site where the endoscope 27 is inserted, that is, as the immovable point.

The pivot $P_1$ is an immovable point set by a second immovable point setter. The second immovable point setter has the same configuration as that of the immovable point setter 11. Accordingly, herein, a detailed description of the second immovable point setter is omitted.

The surgical robot 1 according to some embodiments uses the input manipulation device of the robot arm 3, in other words, of the arm drive device 9 to transmit the command signal to the second arm drive device. Specifically, the surgical robot is provided with a selector switch.

The selector switch enables an output destination of the command signal to be switched between the arm drive device 9 and the second arm drive device. A surgical operator manipulates the selector switch, thereby to switch the operation between the operation of the robot arm 3 and the operation of the second robot arm.

<Input Operation Device>

The master-side input manipulation device is an example of an input device that is directly manipulated by the surgical operator such as a doctor. The input manipulation device is provided with a manipulation force regulating device and a manipulation amount regulating device.

The manipulation force regulating device is a device for regulating a magnitude of a manipulation force. The manipulation amount regulating device is a device for regulating a ratio of an "amount of movement of the robot arm 3" to an "amount of direct manipulation by the surgical operator" (hereinafter, also referred to as "manipulation ratio").

The manipulation force is a force that the user is required to exert on the input manipulation device when the user manipulates the input manipulation device. That is, when a force that the user exerts on the input manipulation device is below the manipulation force, the treatment tool 7 is not displaced, and thus the hand part is not operated.

The magnitude of the manipulation force is a sum of, at least, a manipulation force during movement and a manipulation force during treatment. The manipulation force during movement is a manipulation force when the treatment tool 7 (in other words, the hand part) does not touch an organ, or the like. The manipulation force during treatment is a force caused by the treatment tool 7 (in other words, the hand part) touching the organ, or the like.

In the surgical robot 1 according to some embodiments, the user may change the magnitude of the manipulation force during movement. Further, the surgical robot 1 according to some embodiments utilizes a force (also referred to as "reaction force") exerted on the treatment tool 7 from the organ, or the like, thereby to determine the magnitude of the manipulation force during treatment, when the treatment tool 7 (including the hand part) touches the organ or the like.

That is, the surgical robot 1 is provided with a reaction force detector that detects the aforementioned reaction force. The input manipulation device determines, as the magnitude of the manipulation force during treatment, a value obtained by multiplying the reaction force detected by the reaction force detector with a reaction force coefficient that is a real number exceeding zero.

In some embodiments, the user may change the reaction force coefficient. The input manipulation device may be provided with a setting section for setting the manipulation force during movement, a setting section for setting the reaction force coefficient, and a setting section for setting the manipulation ratio. The setting sections are operated and set by the user.

2. Details of Immovable Point Setter

The immovable point setter 11 according to some embodiments may execute a position recognition function and a memory function. The immovable point setter 11 utilizes the position recognition function and the memory function to memorize the position of the pivot P1 as an immovable point.

The position recognition function is a function to recognize a distal end position of the treatment tool 7 held by the robot arm 3. The memory function memorizes, as the pivot $P_1$, the distal end position recognized by the position recognition function.

The position recognition function according to some embodiments acquires or computes a coordinate, or the like that indicates the distal end position of the treatment tool 7 based on an attitude of the robot arm 3, whereby the distal end position of the treatment tool 7 is recognized by the position recognition function. The memory function memorizes the coordinate as the pivot $P_1$. The pivot $P_1$ memorized by the memory function may be, for example, a position recognized by the position recognition function. In addition, the position recognized by the position recognition function is not limited to the distal end position of the surgical instrument 7. The position recognized by the position recognition function may be, for example, an incision position that is a position of a site where the trocar 15 is to be inserted in surgery.

It is to be noted that, when the immovable point setting is performed, an equivalent to the surgical instrument may be used, instead of the treatment tool 7. The equivalent to the surgical instrument is a member having a shape similar to that of the treatment tool 7. Specifically, for example, in some embodiments, a rod-shaped or pipe-shaped member, or the like may correspond to the equivalent to the surgical instrument. In addition, in the case of the second immovable point setter, the endoscope 27 corresponds to the equivalent to the surgical instrument.

The position recognition function and memory function according to some embodiments are implemented by software, programs constituting the software, and a microcomputer. The microcomputer comprises a CPU, a ROM, and a RAM to run the software. The software is stored in a non-volatile storage section in advance.

As shown in FIG. 2, the surgical robot 1 comprises a setting button 17A and a free displacement enabling button 17B. The setting button 17A and the free displacement enabling button 17B are provided on at least one of the robot arm 3 and the control device 5. The robot arm 3 corresponds to an example of a slave device, and the control device 5 corresponds to an example of a master-side device.

The setting button 17A is an example of a setting operating section operated by the user. Herein, the user is a person that performs the immovable point setting, specifically, a surgical operator, or those who assist surgery. When the setting button 17A is manipulated, the immovable point setting mode starts or ends.

In other words, when the setting button 17A is manipulated not in the immovable point setting mode, the immovable point setting mode starts. When the setting button 17A is manipulated in the immovable point setting mode, the immovable point setting mode ends.

Specifically, in a case in which the setting button 17A is pressed down for a time exceeding a preset time (for example, three seconds), the immovable point setting mode starts. Once the immovable point setting mode starts, the position recognition function may be placed into an executable state.

When the setting button 17A is pressed down for a time shorter than the preset time (for example, two seconds), the position recognition function is executed, and then the memory function is executed. Thereafter, the pivot $P_1$ is memorized as the immovable point, and then the immovable point setting mode ends.

The free displacement enabling button 17B is an example of an operating section operated by the user. When the free displacement enabling button 17B is manipulated, the arm drive device 9 becomes a free displacement mode. The free displacement mode is a mode in which the robot arm 3 may be freely displaced in accordance with the external force acting on the robot arm 3.

Thus, during the free displacement mode, the user may press or pull the robot arm 3, whereby the robot arm 3 may be freely displaced. That is, during the free displacement mode, the user may press or pull the robot arm 3 without manipulating the master-side input manipulation device, thus enabling a distal end of the treatment tool 7 to match the incision position.

The free displacement mode ends when the free displacement enabling button 17B is manipulated in the free displacement mode or when the immovable point setting mode ends. Even if the external force acts on the robot arm 3 in a state in which the free displacement mode is not executed, the robot arm 3 is not displaced.

<Control in Immovable Point Setting Mode>

Figure 4:
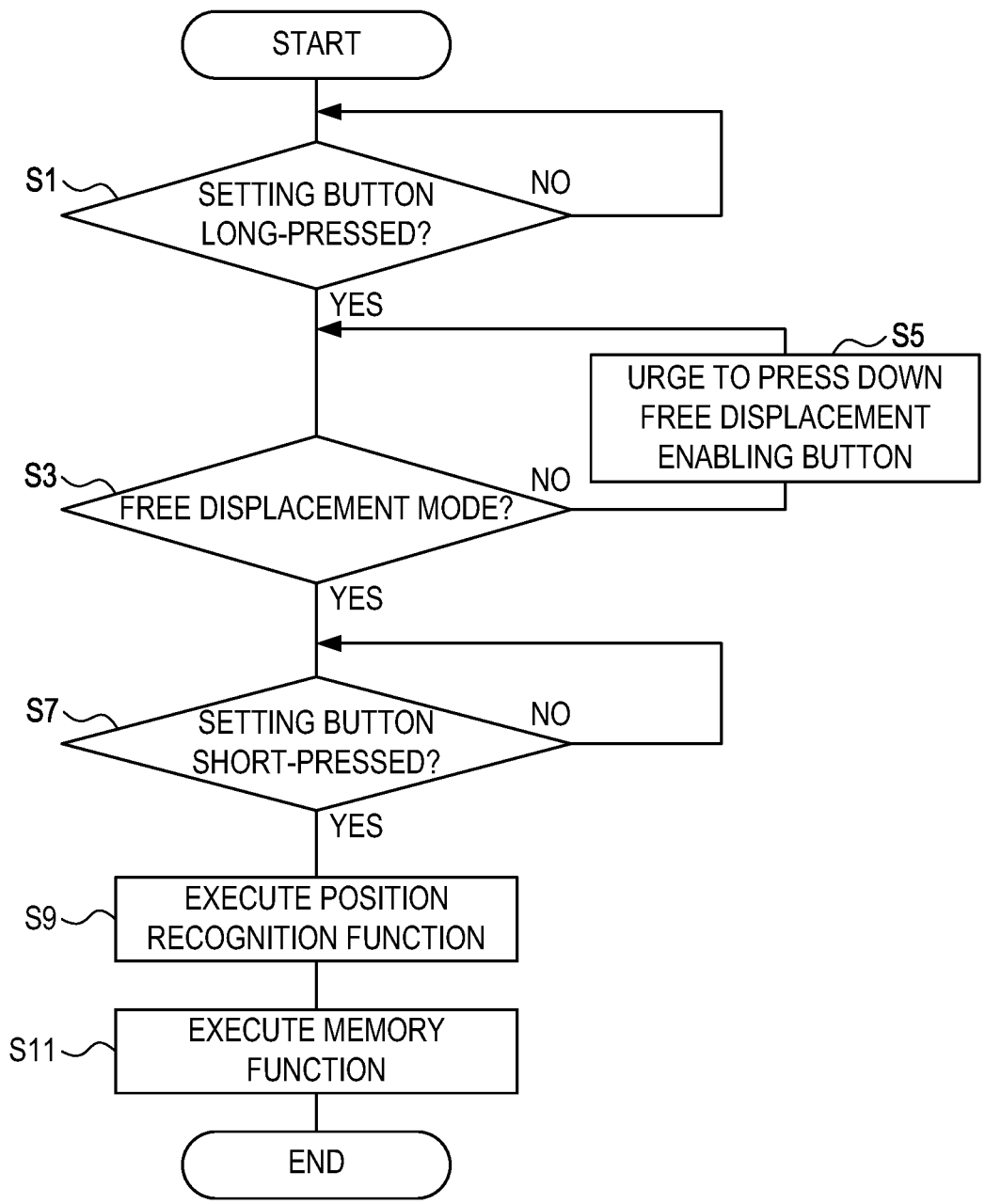
FIG. 4 is a flowchart showing a control of an immovable point setting mode of the surgical robot according to some embodiments.

FIG. 4 is a flowchart showing a control of an immovable point setting mode of the surgical robot according to some embodiments. FIG. 4 shows an example control of the control device 5 executed in the immovable point setting mode. The control device 5 determines whether the setting button 17A is continuously pressed down for a time exceeding the preset time (for example, three seconds) (S1). It is to be noted that "(S1)" and, the like indicate control step numbers shown in FIG. 4.

The control device 5, when determining that the setting button 17A is not pressed down for more than the preset time (S1: NO), continues to monitor whether the setting button 17A is depressed, i.e., the process returns to S1. If the control device 5 determines that the setting button 17A is continuously pressed down for a time exceeding the preset time (S1: YES), the control device 5 determines whether the arm drive device 9 is in the free displacement mode (S3).

If the control device 5 determines that the arm drive device 9 is not in the free displacement mode (S3: NO), the control device 5 urges the user to manipulate the free displacement enabling button 17B by using notification means such as sounds (for example, buzzer), a warning light, or the like (S5), and the process returns to S3.

If the control device 5 determines that the arm drive device 9 is in the free displacement mode (S3: YES), the control device 5 determines whether the setting button 17A is pressed down for a time shorter than the preset time (for example, two seconds) (S7).

The control device 5, when determining that the setting button 17A is not pressed down for less than the preset time (S7: NO), returns to S7. If the control device 5 determines that the setting button 17A is pressed down for a time shorter than the preset time (S7: YES), the control device 5 executes the position recognition function (S9), and then executes the memory function (S11).

That is, in some embodiments, if the arm drive device 9 is not in the free displacement mode (S3: NO), the position recognition function and the memory function are placed into a practically non-executable state.

Further, after memorizing the pivot $P_1$ as the immovable point, the control device 5 ends the immovable point setting mode and the free displacement mode, and notifies the user that the pivot $P_1$ is memorized as the immovable point.

3. Notification of Information

The first display section 19 and the second display section 25 shown in FIG. 2 are monitors that transmits information such as textual information, image information, and the like, to the user. On the first display section 19, at least information related to the surgical robot 1 (hereinafter, also referred to as state information) is displayed. On the second display section 25, an image captured by the endoscope 27 is displayed.

The endoscope 27 according to some embodiments may be configured by a camera such as a stereo camera and the like, which is capable of capturing images of a three-dimensional object. The captured image processor 25A is a processor for displaying stereoscopic images on the second display section 25.

<Display of First State Information>

The first display processor 21A and the second display processor 21B cause the first display section 19 to display information. The first display processor 21A causes the first display section 19 to display the incision position, that is, a relative positional relationship between the pivot $P_1$ and the distal end position of the treatment tool 7.

The first display processor 21A according to some embodiments causes the relative positional relationship to be represented by using image information such as symbols (for example, icons), and the like. Each icon is a symbol indicating the corresponding pivot $P_1$ and distal end position of the treatment tool 7.

Figure 5C:
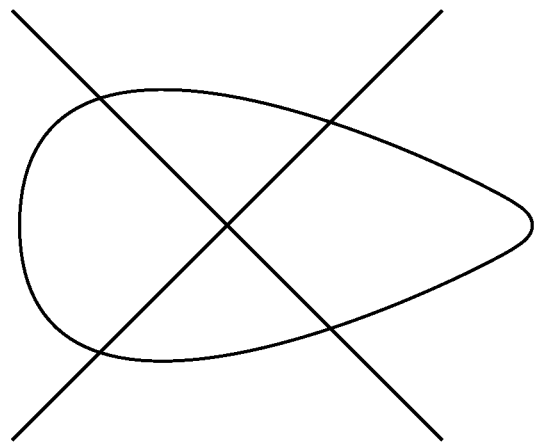
FIG. 5C is a diagram showing a display example of the first state display.
Figure 5B:
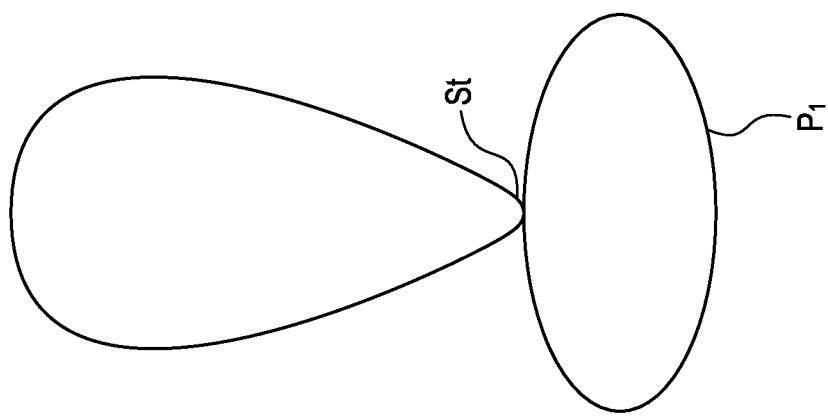
FIG. 5B is a diagram showing a display example of the first state display.
Figure 5A:
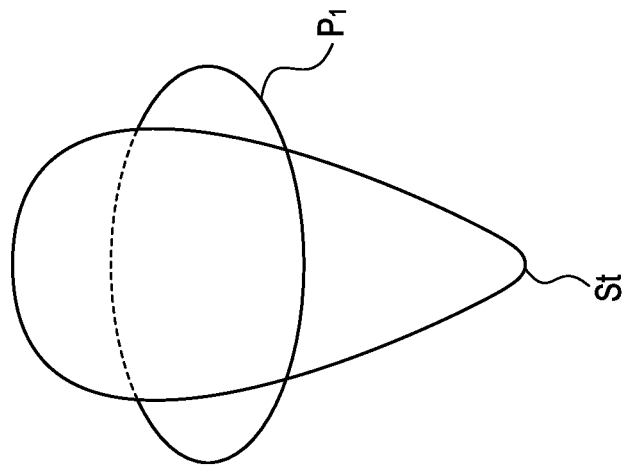
FIG. 5A is a diagram showing a display example of a first state display.

FIG. 5A to 5C are diagrams showing display examples of a first display state. Specifically, for example, FIG. 5A shows a case in which a distal end position St of the treatment tool 7 relative to the pivot $P_1$ is positioned inside a body of a patient. FIG. 5B shows a case in which the distal end position St of the treatment tool 7 relative to the pivot $P_1$ is positioned outside the body of the patient. FIG. 5C shows a state in which the immovable point setting is not performed yet.

The second display processor 21B causes the first display section 19 to display a detection result obtained by a drape detector 23 (see FIG. 2). The drape detector 23 detects whether the drape 20 is mounted on the robot arm 3. The drape detector 23 is provided on the robot arm 3.

Figure 6B:
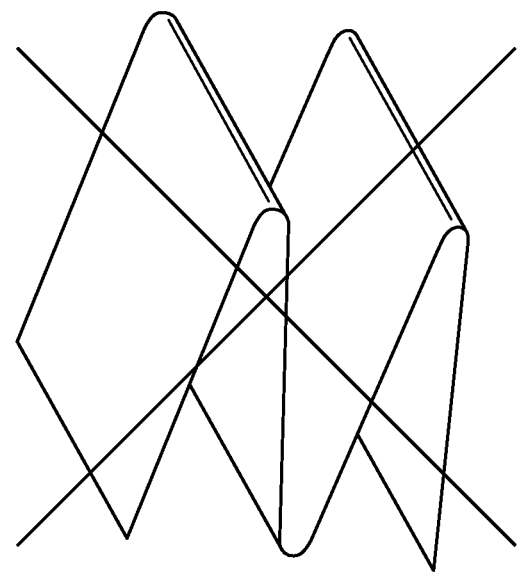
FIG. 6B is a diagram showing a display example of the first state display.
Figure 6A:
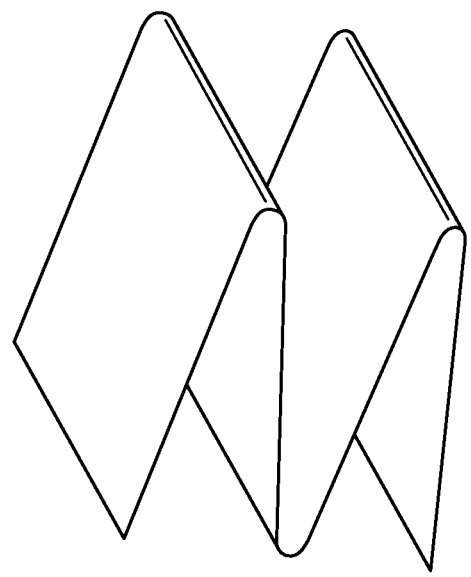
FIG. 6A is a diagram showing a display example of the first state display.

FIGS. 6A and 6B are diagrams showing display examples of the first display state. If the drape 20 is mounted on the robot arm 3, the second display processor 21B causes the first display section 19 to display information (for example, see FIG. 6A) indicated that the drape 20 is attached to the robot arm 3. If the drape 20 is not mounted on the robot arm 3, the second display processor 21B causes the first display section 19 to display information (for example, see FIG. 6B) indicating that the drape 20 is not attached to the robot arm 3.

<Display of Second State Information>

The third display processor 29 causes the first display section 19 to display a relative positional relationship between the distal end position of the treatment tool 7 and a tip position of the endoscope 27. That is, the third display processor 29 may execute at least three functions.

Specifically, a first function is an acquisition function of acquiring information on the distal end position of the treatment tool 7. A second function is a calculation function of calculating positional information on the tip position of the endoscope 27. A third function is a displaying function of causing the first display section 19 to display information on the distal end position of the treatment tool 7 and on the tip position of the endoscope 27. The third display processor 29 according to some embodiments utilizes the position recognition function to implement the first function and second function.

Figure 7:
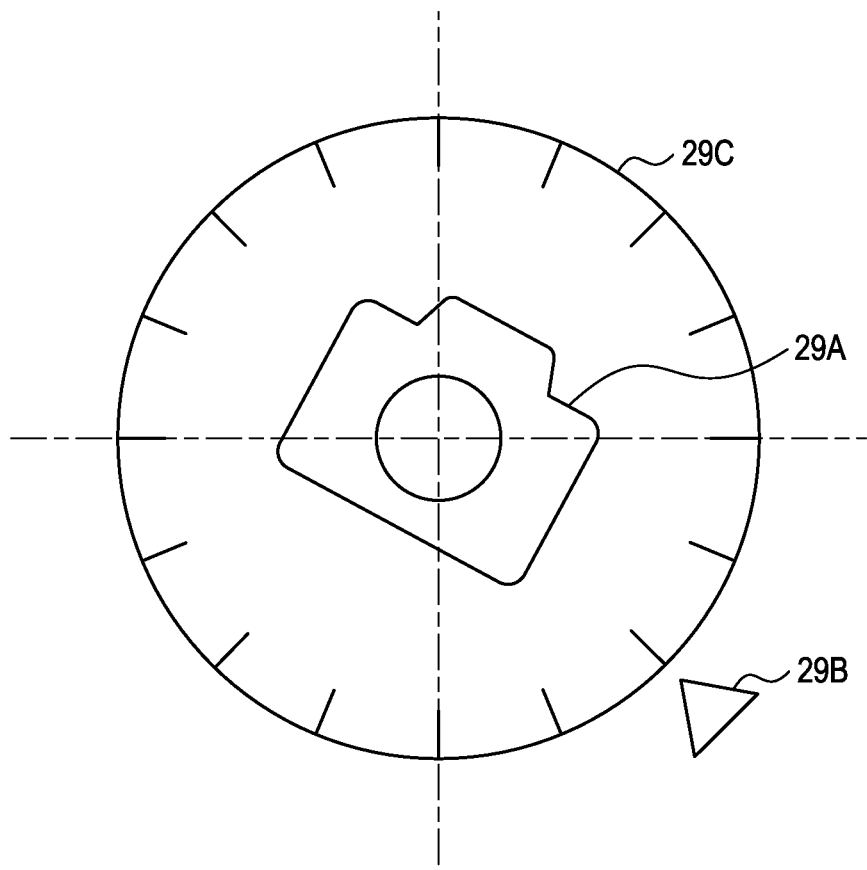
FIG. 7 is a diagram showing a display example of a second state display.

FIG. 7 is a diagram of a display example of a second state display. The third display processor 29 utilizes the calculation result of the calculation function of calculating positional information, thereby to represent the a relative positional relationship between the distal end position of the treatment tool 7 and the tip position of the endoscope 27. Specifically, as shown in FIG. 7, at least, a symbol (for example, an icon) 29B indicating the distal end of the treatment tool 7 and a symbol (for example, an icon) 29A indicating a tip portion of the endoscope 27 are displayed on the first display section 19.

Further, the first display section 19 displays not only the two types of the icons 29A and 29B, but also a full-circle protractor 29C with a reference position based on the tip position of the endoscope 27. The full-circle protractor 29C may be displayed in a state in which the center of the full-circle protractor 29C matches the center of a display screen of the first display section 19.

The center of the display screen of the first display section 19 may indicate the physical center of the display screen when the second state information only is displayed on the first display section 19. If other information (for example, the first state information), addition to the second state information, is also displayed on the first display section 19, the center of the display screen of the first display section 19 may indicate a central display area of the second state information display area.

In the surgical robot 1 according to some embodiments, the center of the display area of the second state information matches the physical center of the display area. Accordingly, if two or more types of state information are displayed, the center of the full-circle protractor 29C matches the physical center of the display screen.

The icon (hereinafter, also referred to as "camera icon") 29A indicating the tip portion of the endoscope 27 is displayed in the center of the display screen. A display form or a display position of the icon 29B indicating the treatment tool 7 varies depending on the relative positional relationship between the distal end position of the treatment tool 7 and the tip position of the endoscope 27.

The display form of the icon 29B may indicate, for example, a specific design of the icon 29B. That is, the specific design of the icon 29B includes a shape, pattern, color of the icon 29B, and combination thereof, a manner in which the specific design is displayed (for example, a blinking display and always-on display), and the like.

An up-down direction on the display screen or in the display area coincides with a vertical direction. The camera icon 29A has a display angle relative to the display screen. The display angle varies depending on a rotational angle of the endoscope 27. That is, when the endoscope 27 rotates, the camera icon 29A also rotates in conjunction with the rotation of the endoscope 27. A center position of the camera icon 29A always conforms to the center of the display screen (for example, the center of the full-circle protractor 29C), regardless of a physical position of the endoscope 27.

<Display of Third State Information>

The third state information is information on whether the treatment tool 7 (in other words, the hand part) is in the operable state, that is, whether the air pressure cylinder 9B is in the operable state.

After determining information to be notified as the third state information, the operation diagnosis device 31 (see FIG. 2) notifies the user of such information in a form of sound information or image information. The operation diagnosis device 31 according to some embodiments causes the first display section 19 to display the information in the form of image information.

As shown in FIG. 3, the surgical robot 1, in particular, the pneumatic actuator 9E of the arm drive device 9, which is equipped in the surgical robot 1, is provided with pressure detectors $PS_1$ and $PS_2$. The pressure detectors $PS_1$ and $PS_2$ each detect a pressure supplied from the pressure generating device 9C to the air pressure cylinder 9B.

The pressure detector $PS_1$ (hereinafter, also referred to as "first pressure sensor $PS_1$") is a pressure sensor that detects a discharge pressure in the pressure generating device 9C. Specifically, the first pressure sensor $PS_1$ detects a pressure at an outlet of an electromagnetic valve 9F that is provided at a discharge of the pressure generating device 9C.

The pressure detector $PS_2$ (hereinafter, also referred to as "second pressure sensor $PS_2$") is a pressure sensor that detects a pressure at an outlet of the electromagnetic control valve 9D. Signals indicating the detected first pressure sensor $PS_1$ and second pressure sensor $PS_2$ are inputted in the operation diagnosis device 31.

Further, if the operation diagnosis device 31 determines that the pressure detected by the first pressure sensor $PS_1$ (hereinafter, also referred to as "first detection pressure") does not meet a first requirement specified in advance, the operation diagnosis device 31 causes the first display section 19 to display information to that effect.

Similarly, if the operation diagnosis device 31 determines that the pressure detected by the second pressure sensor $PS_2$ (hereinafter, also referred to as "second detection pressure") does not meet a second requirement specified in advance, the operation diagnosis device 31 causes the first display section 19 to display information to that effect.

The second requirement may be or may not be identical to the first requirement. In some embodiments, the first and second requirements are identical. Specifically, these requirements are that "the detected pressure is not equal to or below a specific pressure continuously for a specified time".

The operation diagnosis device 31, which is the controller that controls an operation of the air pressure cylinder 9B (in other words, the electromagnetic control valve 9D), executes the aforementioned determination before the drive controller 13 is activated or when the drive controller 13 is activated.

Figure 8:
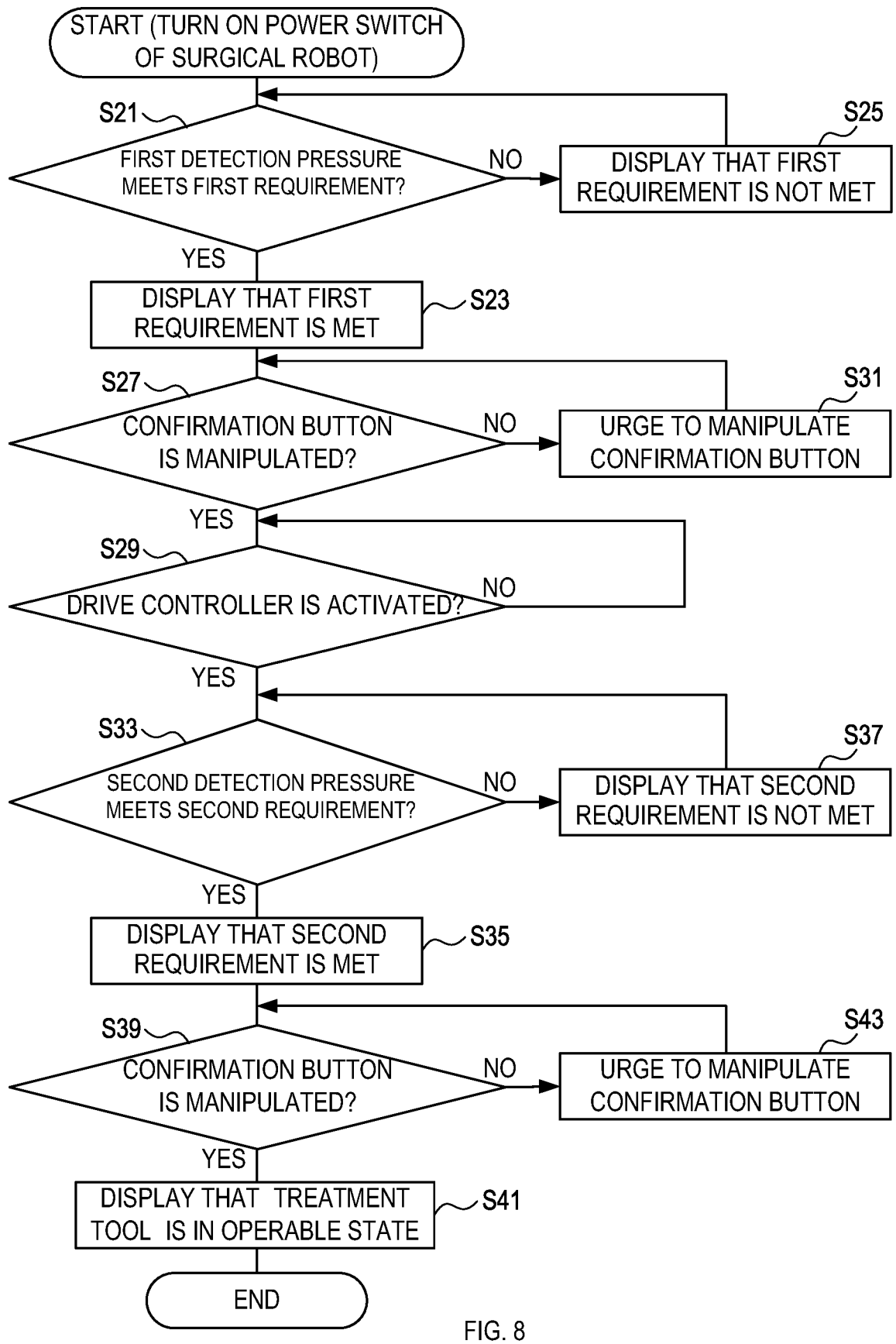
FIG. 8 is a flowchart showing an operation example of an operation diagnosis device according to some embodiments.

FIG. 8 is a flowchart showing an operation example of an operation diagnosis device according to some embodiments. Specifically, the operation diagnosis device 31 executes a control flow shown in FIG. 8. The operation diagnosis device 31 is configured by a microcomputer. A program for executing the control flow is memorized in advance in the non-volatile storage section.

In the surgical robot 1 according to some embodiments, a power switch of the pressure generating device 9C is provided separately from a power switch of the surgical robot 1, and also the power switch of the pressure generating device 9C and the power switch of the surgical robot 1 are not interlinked. Accordingly, at the time of turning on the power switch of the surgical robot 1, there is a possibility that the pressure generating device 9C may fail to reach an operable state.

Therefore, when the power switch of the surgical robot 1 is turned on, the operation diagnosis device 31 determines whether the first detection pressure meets the first requirement (S21), as shown in FIG. 8. It is to be noted that "(S21)", and the like, indicate control operations numbers shown in FIG. 8.

Further, if the operation diagnosis device 31 determines that the first requirement is met (S21: YES), the operation diagnosis device 31 causes the first display section 19 to display that the first requirement is met (S23). If the operation diagnosis device 31 determines that the first requirement is not met (S21: NO), the operation diagnosis device 31 causes the first display section 19 to display that the first requirement is not met (S25).

After executing S23, the operation diagnosis device 31 determines whether a confirmation button is manipulated (S27). The confirmation button is an example of an input section operable by the user, and is a physical switch or a virtual switch that is displayed on a touchscreen panel.

If the operation diagnosis device 31 determines that the confirmation button is not manipulated (S27: NO), the operation diagnosis device 31 notifies the user of information that urges the user to manipulate the confirmation button (S31). The information may be, for example, a sound or an image. The image indicating the information to be notified may include a character or letter.

If the operation diagnosis device 31 determines that the confirmation button is manipulated (S27: YES), the operation diagnosis device 31 determines whether the drive controller 13 is activated (S29). If the operation diagnosis device 31 determines that the drive controller 13 is activated (S29: YES), the operation diagnosis device 31 determines the second detection pressure does meet the second requirement (S33).

If the operation diagnosis device 31 determines that the second requirement is met (S33: YES), the operation diagnosis device 31 causes the first display section 19 to display that the second requirement is met (S35). If the operation diagnosis device 31 determines that the second requirement is not met (S33: NO), the operation diagnosis device 31 causes the first display section 19 to display that the second requirement is not met (S37).

After executing S35, the operation diagnosis device 31 determines whether the confirmation button is manipulated (S39). If the operation diagnosis device 31 determines that the confirmation button is not manipulated (S39: NO), the operation diagnosis device 31 notifies the information that urges the user to manipulate the confirmation button (S43). If the operation diagnosis device 31 determines that the confirmation button is manipulated (S39: YES), the operation diagnosis device 31 causes the first display section 19 to display that the treatment tool 7 is in the operable state (S41), and the operation diagnosis device 31 ends this control flow.

5. Features of Surgical Robot According to Some Embodiment

The surgical robot 1 according to some embodiments utilizes a pressure detected by the first pressure sensor $PS_1$ and the second pressure sensor $PS_2$ to determine whether the air pressure cylinder 9B is in the operable state, and also notify the result of the determination. This enables the user to readily know whether the surgical robot 1 is in the operable state.

The operation diagnosis device 31 may execute the aforementioned determination when the drive controller 13 is activated or before an activation operation is performed. This enables the surgical operator to readily know whether the surgical robot is in the operable state, when the surgical operator starts surgery.

In the surgical robot 1 according to some embodiments, the relative positional relationship between the distal end of the treatment tool 7 and the tip portion of the endoscope 27 is displayed on the first display section 19. Thus, in the surgical robot 1, the surgical operator may easily deal even with the case where the distal end position of the treatment tool 7 deviates from the imaging region.

In an example embodiment, the monitor (for example, the first display section 19) to display the state information is separately provided from the monitor (for example, the second display section 25) to display the image captured by the endoscope 27. This facilitates surgery by the surgical operator.

If, in addition to the image captured by the endoscope 27 (hereinafter, also referred to as "captured image"), the state information is also displayed on the second display section 25, it becomes difficult for the surgical operator to perform surgery since the display of the state information partly hides the captured image.

In some embodiments, together with the positional relationship of the two types of icons 29A and 29B, the full-circle protractor 29C with a reference position base on the distal end position of the treatment tool 7 is displayed on the first display section 19. This allows the surgical operator to easily grasp the distal end position of the treatment tool 7.

In some embodiments, in a state in which the center of the full-circle protractor 29C coincides with the center of the display screen of the first display section 19, the icon 29A representing the tip portion of the endoscope 27 is displayed in the center of the display screen. In accordance with changes in the positional relationship, the display form of the icon 29B representing the treatment tool 7 or the display position of the icon 29B changes. This allows the surgical operator to easily grasp the distal end position of the treatment tool 7.

In some embodiments, the up-down direction on the display screen coincides with the vertical direction. This allows the surgical operator to easily grasp the distal end position of the treatment tool 7.

In the surgical robot 1 according to some embodiments, the relative positional relationship between the site where the trocar 15 is to be inserted during surgery and the distal end position of the treatment tool 7 is displayed on the first display section 19. This allows the surgical operator to confirm "whether the treatment tool 7 is moving such that the portion of the treatment tool 7 corresponding to the incision site remains stationary".

In other words, whether the surgical robot 1 "has recognized the site where the trocar 15 is to be inserted as the immovable point", that is, whether surgery by the surgical robot 1 is ready to be performed may be easily and reliably recognized by the surgical operator.

The first display processor 21A utilizes the position memorized by the immovable point setter 11 as the site where the trocar 15 is to be inserted. This allows the surgical operator to easily and reliably recognize whether the immovable point setter 11 memorizes the incision position as the immovable point.

In the surgical robot 1 according to some embodiments, the detection result of the drape detector 23 is displayed on the first display section 19. This allows the surgical operator to easily and reliably recognize whether surgery by the surgical robot 1 is ready to be performed.

The surgical robot 1 according to some embodiments recognizes the position of the site where the trocar 15 is to be inserted during surgery, that is, the incision position, and memorizes the recognized position as the pivot $P_1$. Thus, in the surgical robot 1, alignment work between the position of the pivot $P_1$ and the incision site may be easily performed.

The arm drive device 9 may execute the free displacement mode. Thus, in the surgical robot 1, the user may perform the position recognition function and the memory function after aligning the distal end of the treatment tool 7 with the incision site. Accordingly, alignment work between the position of the pivot $P_1$ and the incision site may be reliably performed.

In the surgical robot 1 according to some embodiments, the manipulation force regulating device is provided for regulating the magnitude of the manipulation force. This inhibits the surgical operator from greatly feeling uncomfortable when manipulating the input manipulation device. Thus, the surgical operator may perform surgery properly.

That is, in surgery using the surgical robot 1, since the surgical operator does not directly manipulate the treatment tool 7 such as forceps, and the like, tactile perception of forceps when touching the organ, or the like may not be transferred to the surgical operator. Thus, it is difficult for the surgical operator to perform precise surgery properly.

However, the surgical robot 1 includes the manipulation force regulating device, so that tactile perception of 0 when they touch the organ, or the like may be reproduced. Accordingly, the surgical operator may perform precise surgery properly.

The surgical robot 1 may change the magnitude of the manipulation force during movement. This enables the surgical operator to manipulate the surgical robot 1 (for example, input manipulation device) without greatly feeling uncomfortable.

In the surgical robot 1, the surgical operator may change the manipulation force during treatment (in other words, the reaction force coefficient). This enables the surgical operator to perform precise surgery properly. Further, the surgical operator may change the manipulation ratio in the surgical robot 1. This enables the surgical operator to perform precise surgery properly.

Other Embodiments

The operation diagnosis device 31 according to the some embodiments may execute the aforementioned determination when the drive controller 13 is activated or before the activation operation is performed. However, a time point when the operation diagnosis device 31 of the present disclosure executes the aforementioned determination is not limited to a time point when the drive controller 13 is activated or before the activation operation is performed.

Specifically, for example, the present disclosure may be configured such that the determination is performed at the time point when the drive controller 13 is activated or before the activation operation is performed, or that the aforementioned determination is made at a time point different from this time point.

In some embodiments, the pressure detector is configured by the first pressure sensor $PS_1$ that detects the discharge pressure in the pressure generating device 9C, and the second pressure sensor $PS_2$ that detects a pressure at the outlet of the electromagnetic control valve 9D. However, the present disclosure is not limited to the configuration including the first pressure sensor $PS_1$ that detects a discharge pressure in the pressure generating device 9C, and the second pressure sensor $PS_2$ that detects a pressure at an outlet of the electromagnetic control valve 9D the pressure generating device 9C.

In some embodiments, the power switch of the pressure generating device 9C and the power switch of the surgical robot 1 are not configured to be interlinked. However, the present disclosure is not limited to the configuration in which the power switch of the pressure generating device 9C and the power switch of the surgical robot 1 are not interlinked. The present disclosure may be configured such that, for example, when the power switch of the surgical robot 1 is turned on, the power switch of the pressure generating device 9C is automatically turned on in conjunction with the power switch of the surgical robot 1.

In some embodiments, the robot arm 3 for holding the treatment tool 7 and the second robot arm for holding the endoscope 27 are provided. However, the present disclosure is not limited to the configuration in which the robot arm 3 for holding the treatment tool 7 and the second robot arm for holding the endoscope 27 are provided.

Specifically, for example, the present disclosure may be configured such that no second robot arm is provided and the endoscope 27 is held by an assistant, or that two or more robot arms 3 are provided for holding two or more treatment tools 7.

In some embodiments, the full-circle protractor 29C with a reference position based on the tip position of the endoscope 27 is displayed on the first display section 19. However, the present disclosure is not limited to the configuration in which the full-circle protractor 29C is displayed on the first display section 19. Specifically, for example, the present disclosure may be configured such that the full-circle protractor 29C is not displayed.

In some embodiments, the up-down direction on the display screen coincides with the vertical direction, and the display form of the icon 29B representing the treatment tool 7 or the display position of the icon 29B changes in accordance with changes in the positional relationship. However, the present disclosure is not limited to the configuration in which the up-down direction on the display screen coincides with the vertical direction, and, in accordance with changes in the positional relationship, the display form of the icon 29B representing the treatment tool 7 or the display position of the icon 29B changes.

The robot arm 3 according to some embodiments is configured by a linkage mechanism that may change the position of the pivot. However, the present disclosure is not limited to the configuration in which the robot arm 3 includes the link mechanism that may change the position of the pivot. Specifically, for example, the present disclosure may be configured such that the pivot (in other words, the immovable point) is immovable relative to the robot body.

In some embodiments, the control device 5 comprises the second display processor 21B. However, the present disclosure is not limited to the control device 5 configured to include the second display processor 21B. Specifically, for example, in the present disclosure, a constituent element other than the control device 5 may include the second display processor 21B, and the second display processor 21B may be omitted.

In some embodiments, if the arm drive device 9 is not in the free displacement mode (S3: NO), the control device 5 disables the position recognition function and the memory function. However, the present disclosure is not limited to the configuration such that, if the arm drive device 9 is not in the free displacement mode in the present disclosure (S3: NO), the control device 5 disables the position recognition function and the memory function.

Specifically, for example, the present disclosure may be configured such that the position recognition function and the memory function are in the executable state even not in the free displacement mode. In this case, the distal end of the treatment tool 7 may be aligned with the incision position using the master-side input manipulation device.

The immovable point setter 11 according to some embodiments acquires the coordinate representing the distal end position of the distal end position of the treatment tool 7 from the attitude of the robot arm 3 to recognize the distal end position. However, the present disclosure is not limited to the configuration in which the immovable point setter 11 acquires the coordinate representing the distal end position of the distal end position of the treatment tool 7 from the attitude of the robot arm 3 to recognize the distal end position. Specifically, for example, the present disclosure may be configured such that the distal end position is recognized by using an image analysis technique using a 3D camera such as a stereo camera, and a depth camera.

In some embodiments, the user recognizes the distal end of the treatment tool 7 or the equivalent to the surgical instrument, in a state in which the distal end is aligned with the incision position, to thereby recognize the incision position. However, the present disclosure is not limited to the configuration in which the user recognizes the distal end of the treatment tool 7 or the equivalent to the surgical instrument, in a state in which the distal end is aligned with the incision position, to thereby recognize the incision position. For example, the present disclosure may be configured such that a laser light is applied to the incision position, and the applied position is recognized by using the image analysis technique.

In some embodiments, when the free displacement enabling button 17B is operated, the free displacement mode is provided. However, the present disclosure is not limited to the configuration in which, when the free displacement enabling button 17B is operated, the free displacement mode is provided. Specifically, for example, the present disclosure may be configured such that the surgical robot 1 automatically transitions to the free displacement mode at the same time as the immovable point setting mode is provided.

In some embodiments, the manipulation force regulating device is provided on the master-side input manipulation device. However, the present disclosure is not limited to the configuration in which the manipulation force regulating device is provided on the master-side input manipulation device. Specifically, for example, the manipulation force regulating device may be configured such that, the manipulation force regulating device is omitted in the master-side input manipulation device, or the master-side input manipulation device may include the manipulation force regulating device or either the manipulation force during movement or the manipulation force during treatment that is generated as a manipulation force.

In the input manipulation device according to some embodiments, the setting section for setting the manipulation force during movement, and the setting section for setting the reaction force coefficient are provided. However, the present disclosure is not limited to the configuration in which the setting section for setting the manipulation force during movement, and the setting section for setting the reaction force coefficient are provided. Specifically, for example, the present disclosure may be configured such that the input manipulation device includes at least one of the two setting sections, in other words, one of which is omitted.

In the surgical robot 1 according to some embodiments, the surgical operator may change the manipulation ratio. However, the present disclosure is not limited to the configuration in which the surgical operator may change the manipulation ratio. Specifically, for example, the present disclosure may be configured such that, the surgical robot 1 has a fixed manipulation ratio, that the manipulation ratio may be automatically changed when detecting that the treatment tool 7 touches an organ, or the like, or that the manipulation ratio may be automatically changed in accordance with the reaction force.

Various embodiments have been described above with reference to the drawings. However, it is to be understood that the present disclosure is not limited to the above embodiments, but various changes and modifications may be made therein without departing from the spirit and scope thereof as set forth in appended claims.

What is claimed is:

1. A surgical robot comprising:
an operating section that receives a pressure from a gas;
a pressure generating device that generates the pressure;
a pressure detector that detects the pressure supplied from the pressure generating device to the operating section; and
an operation diagnosis device that determines whether the pressure detected by the pressure detector meets a first pressure requirement, determines, based on the pressure meeting the first pressure requirement and a button being manipulated, whether a driver controller is activated, determines, in response to the driver controller being activated, whether the pressure detected by the pressure detector meets a second pressure requirement, and, in response to the pressure meeting the second pressure requirement and the button being manipulated notifies that the pressure generating device is operable.

2. The surgical robot according to claim 1, further comprising:
a display;
wherein the operation diagnosis device notifies the result by displaying the result of the determinations on the display.

3. A surgical robot comprising:
a pressure generating device that generates a pressure;
a pressure cylinder that receives the pressure from the pressure generating device;
a pressure sensor that detects the pressure supplied from the pressure generating device to the pressure cylinder;
a monitor; and
hardware logic or at least one processor configured to determine whether a first detected pressure meets a first pressure requirement, determine, based on the first detected pressure meeting the first pressure requirement, whether a driver controller is activated, determine, based on the determination that the drive controller is activated, whether a second detected pressure meets a second pressure requirement, and display, on the monitor, a notification based on a result of the determinations.

4. The surgical robot according to claim 3, wherein each pressure requirement is each corresponding detected pressure being not equal to or below a specified pressure.

5. The surgical robot according to claim 4, wherein when the first detected pressure meets the first pressure requirement, the notification indicates that the first pressure requirement has been met.

6. The surgical robot according to claim 5, wherein when the first detected pressure does not meet the first pressure requirement, the notification indicates that the first pressure requirement has not been met.

7. The surgical robot according to claim 4, wherein when the second detected pressure does not meet the second pressure requirement, the notification indicates that the second pressure requirement has not been met.

8. A surgical robot comprising:
a pressure generating device that generates a gas pressure;
a pressure cylinder that receives the gas pressure
a first sensor and a second sensor that detect the gas pressure supplied from the pressure generating device to the pressure cylinder;
a display; and
hardware logic or at least one processor configured to at least:
determine whether a first pressure detected by the first sensor meets a first pressure requirement,
determine, based on the first pressure meeting the first pressure requirement and a confirmation button being manipulated, whether a driver controller is activated, determine, based on the determination of the driver controller being activated, whether a second pressure detected by the second sensor meets a second pressure requirement, and display, on the display based on the second pressure meeting the second pressure requirement and the confirmation button being manipulated, a notification that the pressure cylinder is operable.

9. The surgical robot according to claim 8, wherein the first pressure requirement is the same as the second pressure requirement.

10. The surgical robot according to claim 8, wherein the first pressure requirement is different than the second pressure requirement.

* * * * *